United States Patent
Butler et al.

(10) Patent No.: US 10,722,393 B2
(45) Date of Patent: Jul. 28, 2020

(54) HAND ORTHOSES

(71) Applicants: Michael S. Butler, St. Charles, IL (US); Matthew J. Butler, St. Charles, IL (US); Zachary I. Butler, St. Charles, IL (US)

(72) Inventors: Michael S. Butler, St. Charles, IL (US); Matthew J. Butler, St. Charles, IL (US); Zachary I. Butler, St. Charles, IL (US)

(73) Assignee: Gizmo Medical LLC, Huntley, IL (US)

( * ) Notice: Subject to any disclaimer, the term of this patent is extended or adjusted under 35 U.S.C. 154(b) by 492 days.

(21) Appl. No.: 15/454,884

(22) Filed: Mar. 9, 2017

(65) Prior Publication Data
US 2017/0258624 A1 Sep. 14, 2017

Related U.S. Application Data

(60) Provisional application No. 62/305,673, filed on Mar. 9, 2016.

(51) Int. Cl.
*A61F 5/058* (2006.01)
*A41D 19/015* (2006.01)
*A41D 13/08* (2006.01)
*A63B 71/14* (2006.01)
*A41D 13/015* (2006.01)

(52) U.S. Cl.
CPC ........ *A61F 5/05866* (2013.01); *A41D 13/015* (2013.01); *A41D 13/081* (2013.01); *A41D 19/01588* (2013.01); *A63B 71/14* (2013.01); *A63B 2209/10* (2013.01); *A63B 2244/00* (2013.01); *A63B 2244/19* (2013.01)

(58) Field of Classification Search
CPC .... A41D 13/08; A41D 19/015; A41D 13/081; A41D 19/01588; A41D 13/0153; A41D 19/01505; A41D 19/01576; A41D 19/01582; A63B 71/14; F41H 1/00; A61F 5/05875; A61F 5/05866
USPC ............. 128/878, 879, 880; 602/21, 22, 62; 2/16, 2.5

See application file for complete search history.

(56) References Cited

U.S. PATENT DOCUMENTS

| 4,781,178 A | * | 11/1988 | Gordon | A61F 5/0118 602/22 |
| 8,216,168 B2 | * | 7/2012 | Farrell | A61F 5/0118 602/20 |
| 2008/0052799 A1 | * | 3/2008 | Yoo | A41D 31/14 2/16 |

* cited by examiner

Primary Examiner — Anna K Kinsaul
Assistant Examiner — Caitlin A Carreiro
(74) Attorney, Agent, or Firm — Bruce B. Bowman

(57) ABSTRACT

Hand orthotics are provided for protecting and/or supporting phalanges, metacarpals and/or ligaments of the hand providing thin, lightweight, moldable devices that form to the digits of and to the hand to provide shock absorption and limited range of motion in flexion and extension movements of the digits of the hand, but mitigate or prevent hyperextension. Each orthotic has several plates of thermal plastic, pre-molded carbon fiber or the like that are generally, if not entirely, inflexible and interlinked through limited range of motion hinges, overlapping, and/or abutting plates that accommodate stability and protection. The plates are contained within, on top, underneath, or permutations of these, a form fitting material (e.g. neoprene or vinyl) to maintain a tight fit to the hand, digits and wrist. A thumb plate is hinged to an upper or lower hand plate of the device and includes a loop for receiving the thumb.

16 Claims, 6 Drawing Sheets

HAND ORTHOSES

CROSS-REFERENCE TO RELATED APPLICATIONS

This U.S. non-provisional patent application claims the benefit of and/or priority under 35 U.S.C. § 119(e) to U.S. provisional patent application Ser. No. 62/305,673 filed Mar. 9, 2016 titled "Orthoses For The Protection And Support Of Digits Of The Hand" the entire contents of which is specifically incorporated herein by reference.

FIELD OF THE INVENTION

The present invention relates to orthotics, particularly upper limb orthotics and, more particularly, to hand orthoses.

BACKGROUND OF THE INVENTION

The hand and wrist is subject to a lot of stress and strain from everyday tasks. Sports, such as but not limited to, mountain biking, motorcycling, snow and water skiing, snowboarding, wakeboarding, and the like, for both amateur and professionals put additional strains on the hand and wrist. Hand and wrist injuries can also occur due to manual labor. A highly common injury to the hand is fracture of the metacarpals. Another is rupture of the ulnar collateral ligament. Other injuries to the phalanges, metacarpals and/or ligaments of the hand and wrist also occur. In view of the above, it would be advantageous to have a device to protect the phalanges, metacarpals and/or ligaments of the hand and the wrist from the above-mentioned and other injuries and/or support the phalanges, metacarpals and/or ligaments of hand and wrist after such injuries have occurred.

It is therefore an object of the present invention to provide a device to protect the phalanges, metacarpals and/or ligaments of the hand from the above-mentioned and other injuries and/or support the phalanges, metacarpals and/or ligaments of the hand after such injuries have occurred.

SUMMARY OF THE INVENTION

Hand orthotics, orthoses or gloves are provided for protecting and/or supporting phalanges, metacarpals and/or ligaments of the hand (i.e. hand orthoses). The present hand orthoses are thin, lightweight, preferably, but not necessarily, moldable devices that form to the digits of and to the hand to provide shock absorption and limited range of motion in flexion and extension movements of the digits of the hand, but mitigate or prevent hyperextension.

Each orthotic, orthosis or glove has several generally inflexible, it not entirely inflexible, preferably, but not necessarily, formable plates of thermal plastic, pre-molded carbon fiber or the like that are interlinked through limited range of motion hinges, overlapping, and/or abutting plates that accommodate stability and protection. The plates are contained within, on top, underneath, or permutations of these, a form fitting material (e.g. neoprene or vinyl) to maintain a tight fit to the hand, digits and wrist. A thumb plate is hinged to an upper or lower hand plate of the device and includes a loop for receiving the thumb.

Each orthotic, orthosis or glove fits under another glove such as a sports glove, whereby the use will be able to wear the orthosis in future activities to aid in preventing hand re-injury, post-operatively, and/or prophylactically.

Each orthotic, orthosis or glove may have gel padding strips or the like at the base of the palm within the device liner to accommodate for shock absorption and potential injury.

In one form, the orthotic, orthoses or glove has one or more fitting straps, tensioning bands or the like that cross the wrist, central palm (e.g. inside the hand and on top), as well as wrap the thumb to ensure a custom fit. The straps or tensioning bands or the like mitigate vibration fatigue and reduce carpal tunnel issues.

Further aspects of the present invention will become apparent from consideration of the drawings and the following description of forms of the invention. A person skilled in the art will realize that other forms of the invention are possible and that the details of the invention can be modified in a number of respects without departing from the inventive concept. The following drawings and description are to be regarded as illustrative in nature and not restrictive.

BRIEF DESCRIPTION OF THE DRAWINGS

The features of the invention will be better understood by reference to the accompanying drawings which illustrate forms of the present invention, wherein.

DETAILED DESCRIPTION OF FORMS OF THE INVENTION

Figure 1:
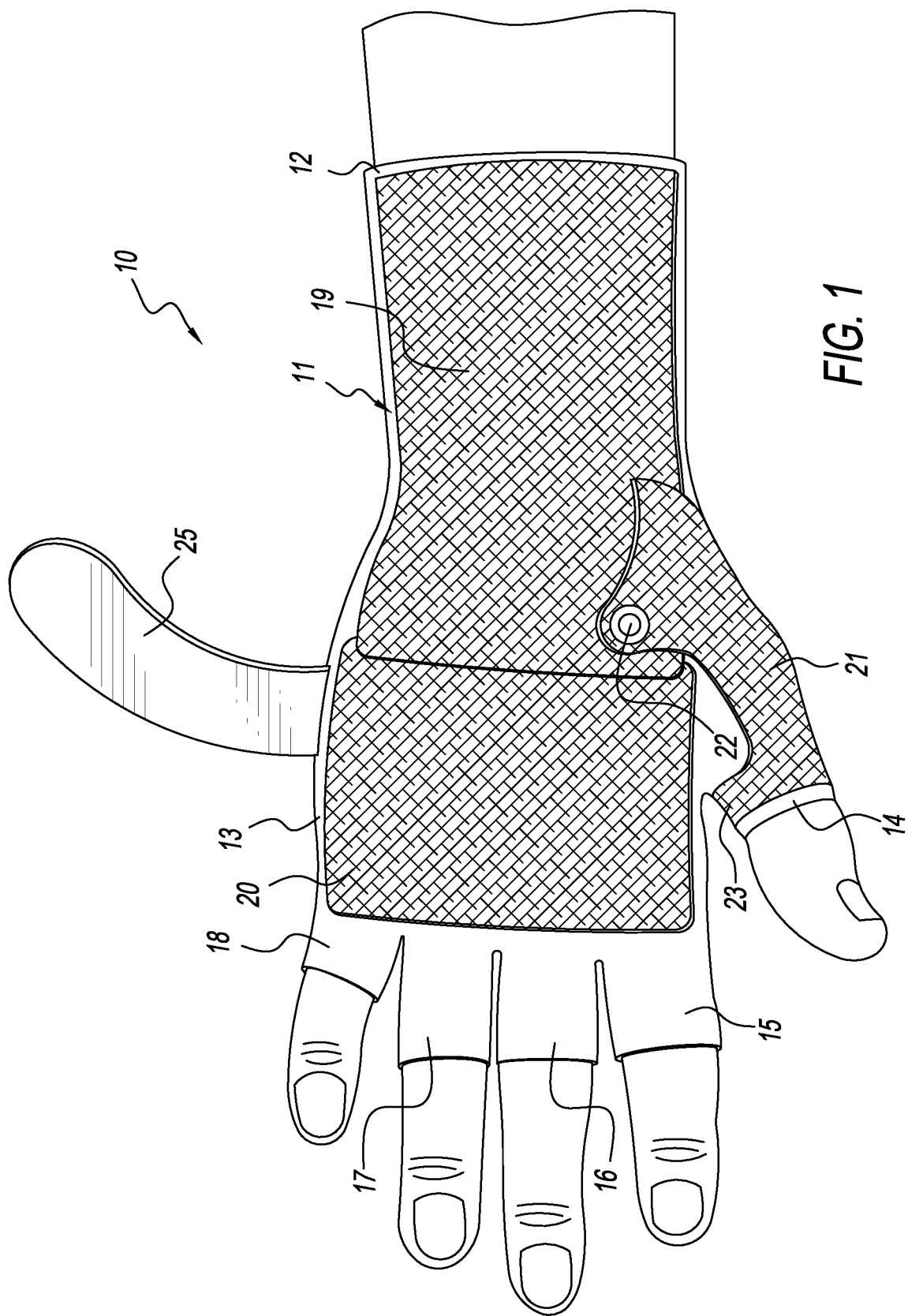
FIG. 1 is a top plan view of the back side of a right hand wearing an exemplary embodiment of a hand orthosis/glove fashioned in accordance with the present principles.
Figure 2:
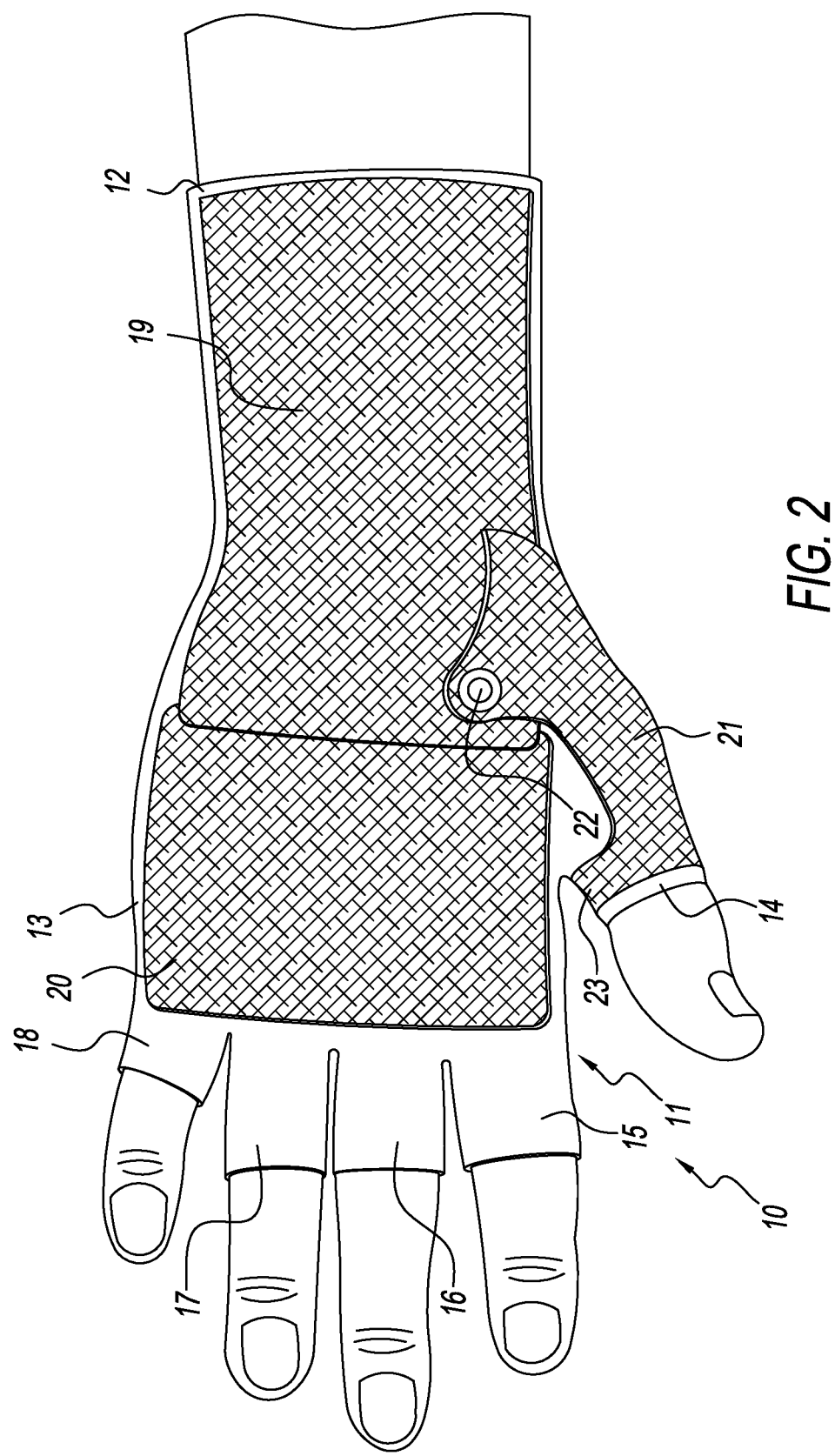
FIG. 2 is a top plan view of the back side of the right hand wearing the hand orthosis/glove of FIG. 1 without a fitting strap.

Referring to FIGS. 1 and 2, there is depicted an exemplary form of a hand orthosis, glove, hand covering, or the like (collectively, "orthosis") generally designated 10 fitted onto a right hand. The hand orthosis 10 is characterized by a body 11 formed of a flexible, but durable, form fitting material such as, but not limited to, neoprene, vinyl, cloth, or the like. The body 11 includes a wrist section 12 that covers the wrist of the hand, a middle section 13 that covers the palm, back and knuckles of the hand, and a digits section covering lower portions of the digits that includes a thumb section 14 that covers a lower portion the thumb, an index finger section 15 that covers a lower portion of the index finger, a middle finger section 16 that covers a lower portion of the middle finger, a ring finger section 17 that covers a lower portion of the ring finger, and a baby (pinky) finger section 18 that covers a portion of the baby finger. Each digit section, 14, 15, 16, 17, 18 may cover more of each digit than shown. Particularly, while each digit section 14, 15, 16, 17, 18 shown as covering the metacarpals, one or more digit section 14, 15, 16, 17, 18 may also cover the phalanges.

FIG. 1 shows a strap, tensioning band or the like (collectively, strap) 25 that may be provided to adjust and/or tighten the body 11 onto the hand. The strap 25 is connected to the palm of the middle section 13 (see FIG. 3) and may utilized a hook and loop material, or otherwise, for securing the free end of the strap 25 to the back side of the middle section 13. FIG. 2 shows the hand orthosis 10 without the strap 25.

A first formable plate 19 of a thermal plastic, pre-molded carbon fiber or the like, is provided within, on top, or underneath the upper side (backside) of the wrist section 12 and partially the middle section 13, the nomenclature "first" being arbitrary. The first plate 19 eliminates, prevents, or hinders hyperextension of the wrist. A second formable plate 20 of a thermal plastic, pre-molded carbon fiber or the like, is provided within, on top, or underneath the middle section 13 at the back side of the hand and shown adjacent the first plate 19, the nomenclature "second" being arbitrary. Preferably, but not necessarily, the first and second plates 19, 20 overlap one another, but may abut or nearly abut one another, may be hinged to one another, or may be otherwise joined to provide stability and protection to the wrist and the carpals (back) of the hand.

A formable thumb plate 21 of a thermal plastic, pre-molded carbon fiber or the like, is provided within, on top, or underneath the thumb section 14. The thumb plate 21 partially surrounds the thumb such that only the outside lateral area of the thumb is covered. A hinge 22 pivotally connects the thumb plate 21 to the first plate 19. The thumb plate 21 has a loop 23 at its distal end that receives the thumb of the wearer. The pivoting thumb plate 21 allows flexion but limits extension so as to eliminate, prevent or hinder hyperextension of the thumb.

FIGS. 1 and 2 depict slightly different sized components of the same hand orthosis 10 illustrating the formable nature of the plates. For instance, the first plates 19 have slightly different lengths. The thumb sections 21 are also slightly different. Additionally, while the digit sections 14, 15, 16, 17, 18 are part of the non-formable body 11, they may also be slightly different to accommodate different dimensioned hands. Otherwise, the components and functions are the same.

Figure 3:
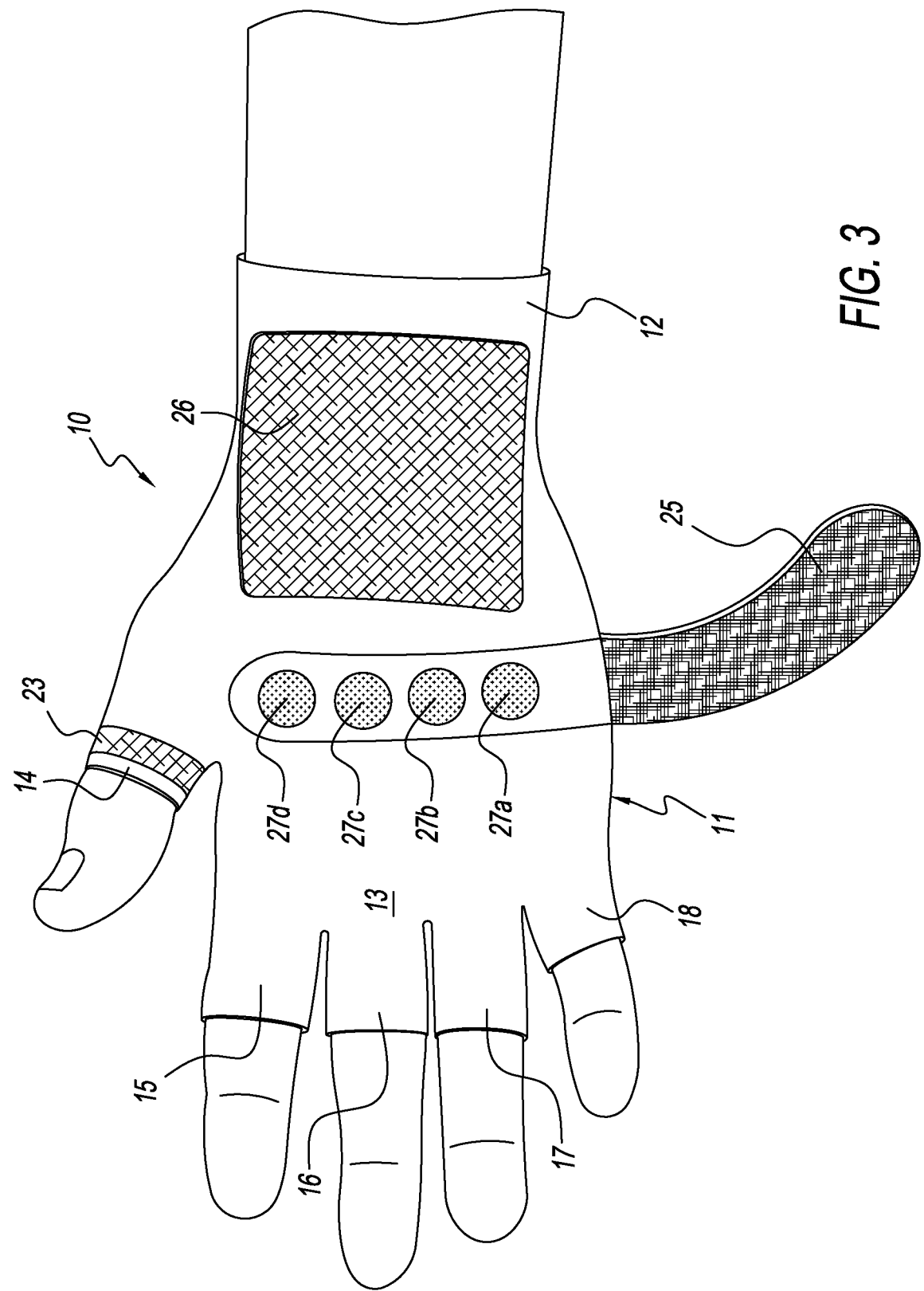
FIG. 3 is a top plan view of the palm side of the right hand wearing the hand orthosis/glove of FIG. 1.

FIG. 3 shows the palm side of the right hand and thus the palm side of the present hand orthosis 10. The hand orthosis 10 has a third formable plate 26 of a thermal plastic, pre-molded carbon fiber or the like, is provided within, on top, or underneath the palm side of the wrist section 12, the nomenclature "third" being arbitrary. Gel pads or inserts 27a, 27b, 27c, 27d are provided on the palm side of the middle section 13 of the body 11. The gel pads 27a, 27b, 27c, 27d aid in reducing vibration and/or fatigue. The strap 25 is also preferably, but not necessarily, anchored to the body 11 in this area.

Figure 4:
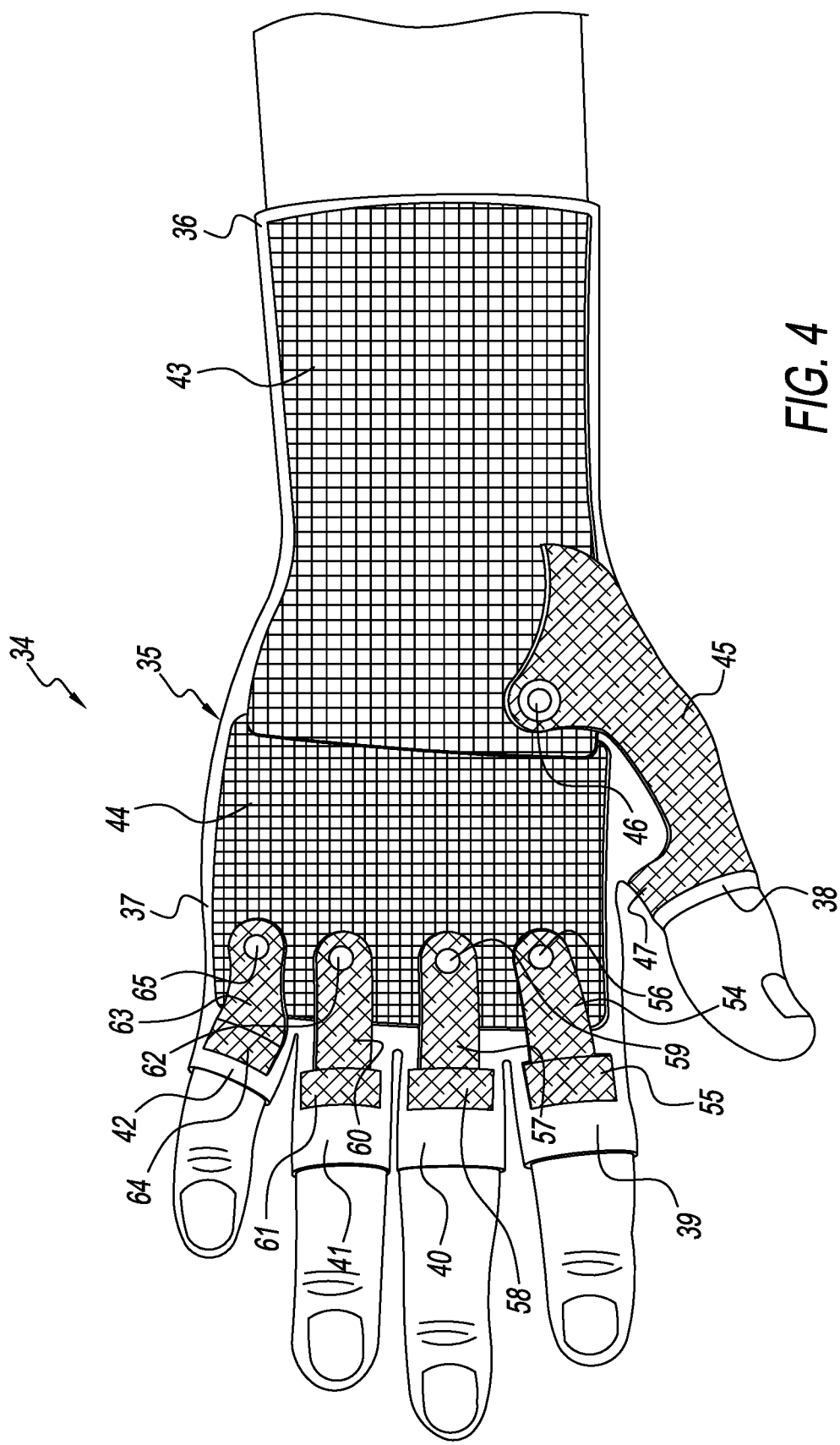
FIG. 4 is a top plan view of the back side of a right hand wearing another exemplary embodiment of a hand orthosis/glove fashioned in accordance with the present principles.
Figure 5:
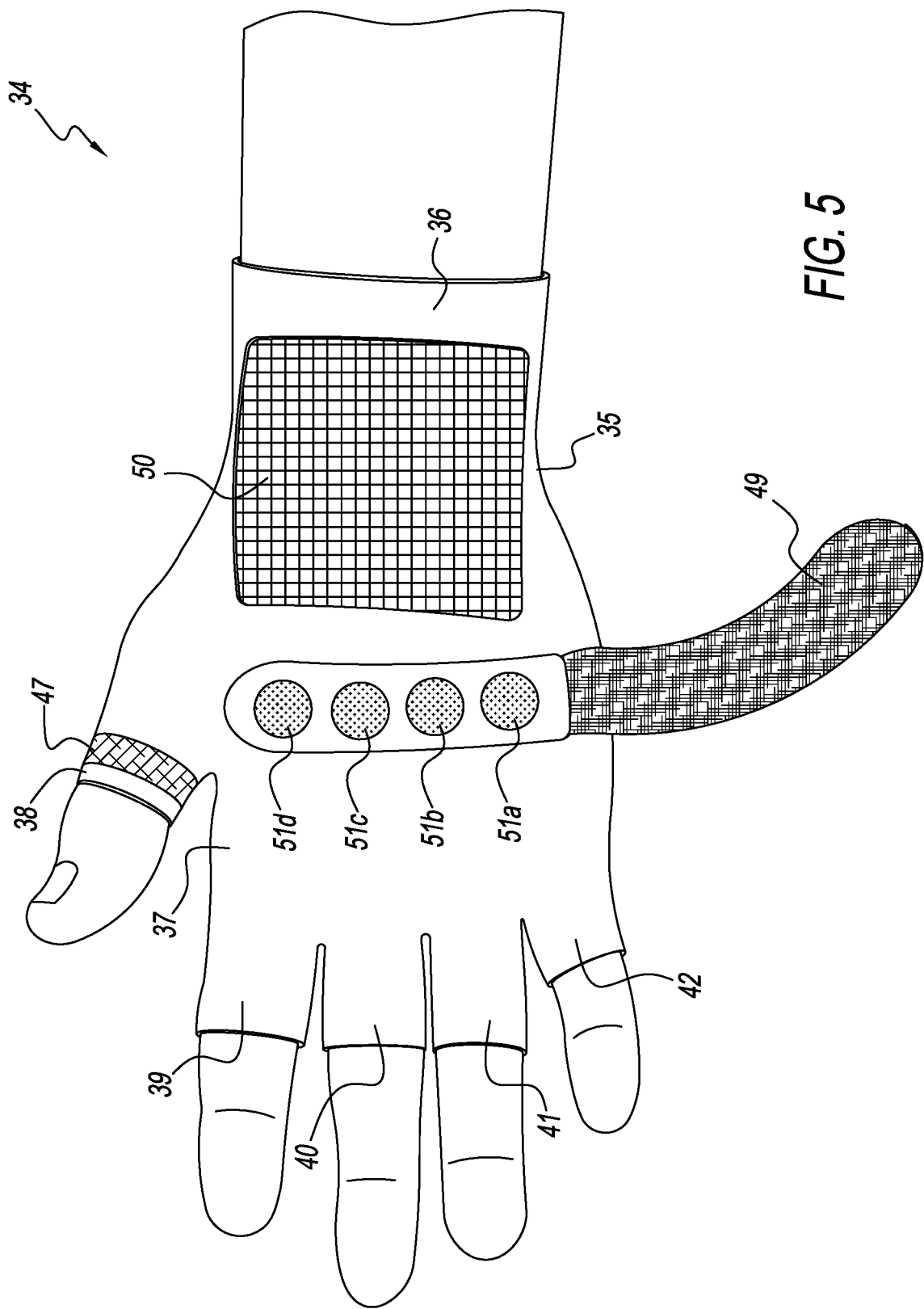
FIG. 5 is a top plan view of the palm side of the right hand wearing the hand orthosis/glove of FIG. 4.

Referring to FIGS. 4 and 5, there is depicted another exemplary form of a hand orthosis, glove, hand covering, or the like (collectively, "orthosis") generally designated 34 fitted onto a right hand. The hand orthosis 34 is characterized by a body 35 formed of a flexible, but durable, form fitting material such as, but not limited to, neoprene, vinyl, cloth, or the like. The body 35 includes a wrist section 36 that covers the wrist of the hand, a middle section 37 that covers the palm, back and knuckles of the hand, and a digits section covering lower portions of the digits that includes a thumb section 38 that covers a lower portion the thumb, an index finger section 39 that covers a lower portion of the index finger, a middle finger section 40 that covers a lower portion of the middle finger, a ring finger section 41 that covers a lower portion of the ring finger, and a baby (pinky) finger section 42 that covers a portion of the baby finger. Each digit section, 38, 39, 40, 41, 42 may cover more of each digit than shown. Particularly, while each digit section 38, 39, 40, 41, 42 shown as covering the metacarpals, one or more digit section 38, 39, 40, 41, 42 may also cover the phalanges.

A strap, tensioning band or the like (collectively, strap) 49 may be provided to adjust and/or tighten the body 37 onto the hand, and thus FIG. 5 shows the strap while FIG. 4 does not. The strap 29 is connected to the palm of the middle section 37 (see FIG. 5) and may utilized a hook and loop material, or otherwise, for securing the free end of the strap 49 to the back side of the middle section 37.

A first formable plate 43 of a thermal plastic, pre-molded carbon fiber or the like, is provided within, on top, or underneath the upper side (backside) of the wrist section 36 and partially the middle section 37, the nomenclature "first" being arbitrary. The first plate 43 eliminates, prevents, or hinders hyperextension of the wrist. A second formable plate 44 of a thermal plastic, pre-molded carbon fiber or the like, is provided within, on top, or underneath the middle section 37 at the back side of the hand and shown adjacent the first plate 43, the nomenclature "second" being arbitrary. Preferably, but not necessarily, the first and second plates 43, 44 overlap one another, but may abut or nearly abut one another, may be hinged to one another, or may be otherwise joined to provide stability and protection to the wrist and the carpals (back) of the hand.

A formable thumb plate 45 of a thermal plastic, pre-molded carbon fiber or the like, is provided within, on top, or underneath the thumb section 38. The thumb plate 45 partially surrounds the thumb such that only the outside lateral area of the thumb is covered. A hinge 46 pivotally connects the thumb plate 45 to the first plate 43. The thumb plate 45 has a loop 47 at its distal end that receives the thumb of the wearer. The pivoting thumb plate 45 allows flexion but limits extension so as to eliminate, prevent or hinder hyperextension of the thumb.

FIG. 5 shows the palm side of the right hand and thus the palm side of the present hand orthosis 34. The hand orthosis 34 has a third formable plate 50 of a thermal plastic, pre-molded carbon fiber or the like, is provided within, on top, or underneath the palm side of the wrist section 36, the nomenclature "third" being arbitrary. Gel pads or inserts 51a, 51b, 51c, 51d are provided on the palm side of the middle section 37 of the body 35. The gel pads 51a, 51b, 51c, 51d aid in reducing vibration and/or fatigue. The strap 49 is also preferably, but not necessarily, anchored to the body 37 in this area.

As seen in FIG. 4, the hand orthosis 34 has a formable index finger plate 54 of a thermal plastic, pre-molded carbon fiber or the like, provided within, on top, or underneath the distal end of the middle section 37 and the proximal end of the index finger section 39. A loop 55 of the formable index finger plate 54 is provided at a distal end thereof that receives the index finger. A hinge 56 pivotally connects the formable index finger plate 54 to the distal end of the second formable plate 44. The hand orthosis 34 also has a formable middle finger plate 57 of a thermal plastic, pre-molded carbon fiber or the like, provided within, on top, or underneath the distal end of the middle section 37 and the proximal end of the middle finger section 40. A loop 58 of the formable middle finger plate 57 is provided at a distal end thereof that receives the middle finger. A hinge 59 pivotally connects the formable middle finger plate 57 to the distal end of the second formable plate 44. The hand orthosis 34 also has a formable ring finger plate 60 of a thermal plastic, pre-molded carbon fiber or the like, provided within, on top, or underneath the distal end of the middle section 37 and the proximal end of the ring finger section 41. A loop 61 of the formable ring finger plate 60 is provided at a distal end thereof that receives the ring finger. A hinge 62 pivotally connects the formable ring finger plate 60 to the distal end of the second formable plate 44. The hand orthosis 34 further has a formable baby (pinky) finger plate 63 of a thermal plastic, pre-molded carbon fiber or the like, provided within, on top, or underneath the distal end of the middle section 37 and the proximal end of the baby finger section 42. A loop 64 of the formable baby finger plate 63 is provided at a distal end thereof that receives the baby finger. A hinge 65 pivotally connects the formable baby finger plate 63 to the distal end of the second formable plate 44.

Figure 6:
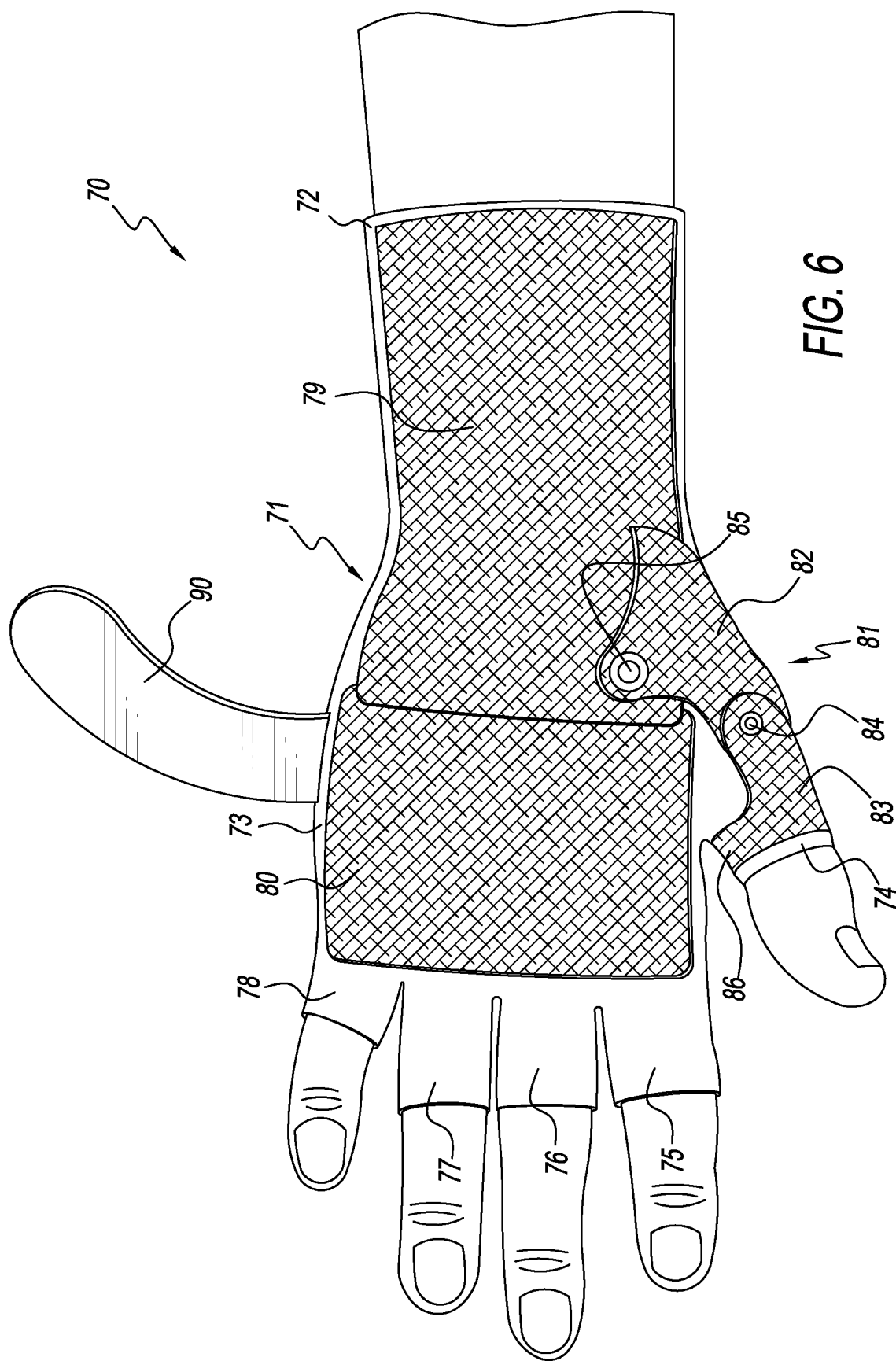
FIG. 6 is a top plan view of the back side of a right hand wearing another exemplary embodiment of a hand orthosis/glove fashioned in accordance with the present principles.

Referring to FIG. 6, there is depicted another exemplary form of a hand orthosis, glove, hand covering, or the like (collectively, "orthosis") generally designated 70 fitted onto a right hand. The hand orthosis 70 is characterized by a body 71 formed of a flexible, but durable, form fitting material such as, but not limited to, neoprene, vinyl, cloth, or the like. The body 71 includes a wrist section 72 that covers the wrist of the hand, a middle section 73 that covers the palm, back and knuckles of the hand, and a digits section covering lower portions of the digits that includes a thumb section 74 that covers a lower portion the thumb, an index finger section 75 that covers a lower portion of the index finger, a middle finger section 76 that covers a lower portion of the middle finger, a ring finger section 77 that covers a lower portion of the ring finger, and a baby (pinky) finger section 78 that covers a portion of the baby finger. Each digit section, 74, 75, 76, 77, 78 may cover more of each digit than shown. Particularly, while each digit section 74, 75, 76, 77, 78 shown as covering the metacarpals, one or more digit section 74, 75, 76, 77, 78 may also cover the phalanges.

A strap, tensioning band or the like (collectively, strap) 90 may be provided to adjust and/or tighten the body 71 about the hand, and thus FIG. 6 shows the strap. The strap 73 is connected to the palm of the middle section 73 (e.g., see FIG. 5) or otherwise, as well as additional straps (not shown) and may utilized a hook and loop material, or otherwise, for securing the free end of the strap 49 to the back side of the middle section 73. Other strap configurations and/or connections may be used and are contemplated.

Preferably, but not necessarily, the first and second plates 19, 20 overlap one another, but may be separate if desired. A first formable plate 79 of a thermal plastic, pre-molded carbon fiber or the like, is provided within, on top, or underneath the upper side (backside) of the wrist section 72 and partially the middle section 73, the nomenclature "first" being arbitrary. The first plate 79 eliminates, prevents, or hinders hyperextension of the wrist. A second formable plate 80 of a thermal plastic, pre-molded carbon fiber or the like, is provided within, on top, or underneath the middle section 73 at the back side of the hand and shown adjacent the first plate 79, the nomenclature "second" being arbitrary. Preferably, but not necessarily, the first and second plates 79, 80 overlap one another, but may abut or nearly abut one another, may be hinged to one another, or may be otherwise joined to provide stability and protection to the wrist and the carpals (back) of the hand.

A formable thumb plate 81 formed by a first section 82 and a second section 83 of a thermal plastic, pre-molded carbon fiber or the like, is provided within, on top, or underneath the thumb section 14. The thumb plate 81 partially surrounds the thumb such that only the outside lateral area of the thumb is covered. Particularly, a hinge 85 pivotally connects the first thumb plate section 82 to the first plate 79, while a hinge 84 pivotally connects the second thumb plate section 83 to the first thumb plate section 82. The second thumb plate section 83 has a loop 86 at its distal end that receives the thumb of the wearer. The pivoting first and second thumb plates 82, 83 allows flexion but limits extension so as to eliminate, prevent or hinder hyperextension of the thumb.

The hand orthosis 70 has a palm side that is similar, if not identical, to the palm side of the right hand as shown in FIG. 3. The hand orthosis 70 has a third formable plate of a thermal plastic, pre-molded carbon fiber or the like, is provided within, on top, or underneath the palm side of the wrist section 72, the nomenclature "third" being arbitrary. Gel pads or inserts are provided on the palm side of the middle section 73 of the body 71. The gel pads aid in reducing vibration and/or fatigue. The strap 90 is also preferably, but not necessarily, anchored to the body 71 in this area.

The formable plates of each of the present hand orthotics, orthoses, or gloves may be generally if not entirely inflexible if desired. Moreover, the formable plates may be non-formable but still generally if not entirely inflexible if desired.

It should be appreciated that dimensions of the components, structures, and/or features of the present hand orthotics/orthoses/gloves may be altered as desired within the scope of the present disclosure.

What is claimed is:

1. An orthotic for the hand comprising:
    a layer of flexible material configured to cover fully a palm of a hand, a back of the hand, a wrist of the hand, a lower section of each finger of the hand, and a lower part of a thumb of the hand;
    a first plate of an inflexible material secured on an outside of the layer of flexible material configured to cover fully the back of the hand and sized to extend about a majority of the back of the hand, the first plate having an upper surface, a first front proximate each finger of the hand, and a first rear opposite the first front;
    a second plate of an inflexible material secured on an outside of the layer of flexible material configured to cover fully an upper part of the wrist of the hand adjacent the back of the hand, the second plate having a lower surface, a second front proximate the first rear of the first plate, and a second rear opposite the second front, the lower surface of a first strip of the second front of the second plate overlapping a second strip of the upper surface of the first plate to inhibit extension of the wrist of the hand;
    a third plate of an inflexible material secured on an outside of the layer of flexible material configured to cover the lower part of the thumb of the hand, the third plate configured to fit about the lower part of the thumb of the hand; and
    a hinge coupling the third plate to the second plate to inhibit extension of the thumb of the hand.

2. The orthotic for the hand of claim 1, wherein the third plate has a loop at an end of the third plate distal the hinge, the loop surrounding a distal end of the flexible material configured to cover fully the thumb of the hand and adapted to be received over an upper part of the thumb of the hand.

3. The orthotic for the hand of claim 2, further comprising:
    a fourth plate of an inflexible material connected by a second hinge to an upper part of the first plate of inflexible material and configured to extend over the index finger of the hand;

a fifth plate of an inflexible material connected by a third hinge to an upper part of the first plate of inflexible material and configured to extend over the middle finger of the hand;

a sixth plate of an inflexible material connected by a fourth hinge to an upper part of the first plate of inflexible material and configured to extend over the ring finger of the hand; and a seventh plate of an inflexible material connected by a fifth hinge to an upper part of the first plate of inflexible material and configured to extend over the pinky finger of the hand.

4. The orthotic for the hand of claim 3, further comprising:

an eighth plate of an inflexible material on an outside of the layer of flexible material configured to cover the palm of the hand.

5. The orthotic for the hand of claim 2, further comprising:

a fourth plate of an inflexible material on an outside of the layer of flexible material configured to cover fully the palm of the hand.

6. The orthotic for the hand of claim 5, further comprising:

a strap attached to the flexible material, the strap having a hook or loop material of a hook and loop fastener; and a swatch of a loop or hook material of the hook and loop fastener opposite to that of the strap on the flexible material covering configured to cover fully the palm of the hand;

the strap allowing cinching of the flexible material across the hand.

7. The orthotic for the hand of claim 1, wherein the third plate of inflexible material on the outside of the layer of flexible material configured to cover the lower part of the thumb includes a secondary plate having a second hinge that pivotally couples the secondary plate to a distal end of the third plate, the secondary plate having a loop at an end of the secondary plate distal the second hinge, the loop surrounding a distal end of the flexible material configured to cover the thumb of the hand and adapted to be received by the thumb of the hand.

8. An orthotic for the hand comprising:

a flexible material configured to cover fully a palm of a hand, a back of the hand, a wrist of the hand, a lower section of each finger of the hand, and a lower part of a thumb of the hand;

a first plate of a formable material affixed on an outside of the flexible material configured to cover fully the back of the hand, and sized to extend about a majority of the back of the hand, the first plate having an upper surface, a first front proximate each finger of the hand, and a first rear opposite the first front;

a second plate of a formable material affixed on an outside of the flexible material configured to cover fully an upper part of the wrist of the hand adjacent the back of the hand, the second plate having a lower surface, a second front proximate the first rear of the first plate, and a second rear opposite the second front, the lower surface of a first strip of the second front of the second plate overlapping a second strip of the upper surface of the first plate to inhibit extension of the wrist of the hand;

a third plate of a formable material affixed on an outside of the flexible material configured to cover the lower part of the thumb of the hand and configured to fit about the lower part of the thumb of the hand; and a hinge coupling the third plate to the second plate to inhibit extension of the thumb of the hand.

9. The orthotic for the hand of claim 8, wherein the third plate of formable material has a loop at an end of the third plate distal the hinge, the loop adapted to be received by the thumb of the hand.

10. The orthotic for the hand of claim 9, further comprising:

a fourth plate of a formable material connected by a second hinge to a first upper part of the first plate of formable material and configured to extend over the index finger of the hand;

a fifth plate of a formable material connected by a third hinge to a second upper part of the first plate of formable material and configured to extend over the middle finger of the hand;

a sixth plate of a formable material connected by a fourth hinge to a third upper part of the first plate of inflexible material and configured to extend over the ring finger of the hand; and a seventh plate of a formable material connected by a fifth hinge to a fourth upper part of the first plate of formable material and configured to extend over the pinky finger of the hand.

11. The orthotic for the hand of claim 10, further comprising:

an eighth plate of a formable material affixed on an outside of the flexible material configured to cover the palm of the hand.

12. The orthotic for the hand of claim 9, further comprising:

a fourth plate of a formable material affixed on an outside of the flexible material configured to cover the palm of the hand.

13. The orthotic for the hand of claim 12, further comprising:

a strap attached to the flexible material, the strap having a hook or loop material of a hook and loop fastener; and a swatch of a loop or hook material of the hook and loop fastener opposite to that of the strap on the flexible material configured to cover the palm of the hand;

the strap allowing cinching of the flexible material across the hand.

14. The orthotic for the hand of claim 8, wherein the third plate of formable material affixed on the outside of the flexible material configured to cover the lower portion of the thumb of the hand includes a secondary plate having a second hinge that pivotally couples the secondary plate to a distal end of the third plate, the secondary plate having a loop at an end of the secondary plate distal the second hinge, the loop surrounding a distal end of the flexible material configured to cover the thumb of the hand and adapted to be received by the thumb of the hand.

15. A glove for limiting movement of the hand, the glove comprising:

a flexible material configured to cover a palm of a hand, a back of the hand, a wrist of the hand, at least a lower portion of each finger of the hand, and at least a lower portion of a thumb of the hand;

a first plate of a rigid material on an outside of the flexible material configured to cover fully the back of the hand and sized to extend about a majority of the back of the hand, the first plate having an upper surface, a first front proximate each finger of the hand, an a first rear opposite the first front;

a second plate of a rigid material on an outside of the flexible material configured to cover fully an upper part of the wrist of the hand adjacent the back of the hand, the second plate having a lower surface, a second front proximate the first rear of the first plate, and a second rear opposite the second front, the lower surface of a first strip of the second front of the second plate overlapping a second strip of the upper surface of the first plate to inhibit extension and flexion of the wrist of the hand;

a third plate of a rigid material on an outside of the flexible material configured to cover the lower portion of the thumb of the hand and formed to fit about the lower portion of the thumb of the hand;

a hinge coupling the third plate of rigid material to the second plate to inhibit extension and flexion of the thumb of the hand; and a loop at an end of the third plate distal the hinge, the loop surrounding a distal end of the flexible material configured to cover the lower portion of the thumb of the hand and adapted to be received by the thumb of the hand.

16. The glove of claim 15, further comprising:

a fourth plate of a rigid material on an outside of the flexible material configured to cover the palm of the hand.

* * * * *